United States Patent
Watts et al.

(10) Patent No.: US 12,377,228 B2
(45) Date of Patent: *Aug. 5, 2025

(54) SYRINGE WITH A PATIENT CONTACT SURFACE

(71) Applicant: Becton, Dickinson and Company, Franklin Lakes, NJ (US)

(72) Inventors: Kevin Watts, Kearney, NE (US); Roger Hoeck, Holdrege, NE (US); Lance Lee Jacobi, Kearney, NE (US); Amit Uday Limaye, Wayne, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/992,115

(22) Filed: Nov. 22, 2022

(65) Prior Publication Data

US 2023/0098397 A1 Mar. 30, 2023

Related U.S. Application Data

(63) Continuation of application No. 16/091,400, filed as application No. PCT/US2017/026510 on Apr. 7, 2017, now Pat. No. 11,571,523.

(Continued)

(51) Int. Cl.
*A61M 5/46* (2006.01)
*A61M 5/178* (2006.01)
(Continued)

(52) U.S. Cl.
CPC ............. *A61M 5/46* (2013.01); *A61M 5/178* (2013.01); *A61M 5/3129* (2013.01); *A61M 5/42* (2013.01);
(Continued)

(58) Field of Classification Search
CPC ...... A61M 5/46; A61M 5/178; A61M 5/3129; A61M 5/42; A61M 5/3287; A61M 5/425;
(Continued)

(56) References Cited

U.S. PATENT DOCUMENTS 6,689,106 B2  10/2004  Bush, Jr. et al.
8,162,886 B2   4/2012  Sadowski et al.
(Continued)

FOREIGN PATENT DOCUMENTS

CN    106232164 A   12/2016
EP      2703028 A1   3/2014
(Continued)

OTHER PUBLICATIONS

International Search Report dated Jun. 21, 2017, which issued in corresponding PCT Patent Applicaiton No. PCT/US2017/026510.
(Continued)

*Primary Examiner* — Michael J Tsai
*Assistant Examiner* — Justin L Zamory
(74) *Attorney, Agent, or Firm* — Dickinson Wright PLLC

(57) ABSTRACT

A syringe and needle hub for a syringe has distal patient-facing side having a surface for contact with the subject's skin during injection. The contact surface is formed by a distal face of a post supporting a cannula and an outer collar surrounding the post. The axial distance between the distal face of the post and the distal face of the collar provided a contact surface with a radius of curvature to control the desired injection. The syringe barrel can have finger flanges extending outwardly where the flanges have a tactile member such as a dimple projecting from a proximal face of the flange and recess in a distal face of the flange.

17 Claims, 12 Drawing Sheets

Related U.S. Application Data

(60) Provisional application No. 62/320,058, filed on Apr. 8, 2016.

(51) Int. Cl.
*A61M 5/31* (2006.01)
*A61M 5/42* (2006.01)
*A61B 90/00* (2016.01)
*A61M 5/32* (2006.01)

(52) U.S. Cl.
CPC ...... *A61B 2090/032* (2016.02); *A61M 5/3287* (2013.01)

(58) Field of Classification Search
CPC ................. A61M 5/349; A61M 5/3137; A61M 2205/582; A61B 2090/032
See application file for complete search history.

(56) References Cited

U.S. PATENT DOCUMENTS

| | | | |
|---|---|---|---|
| 9,283,330 B2 | 3/2016 | Wase et al. | |
| 9,445,838 B2* | 9/2016 | Wei | A61M 5/329 |
| 2003/0050602 A1* | 3/2003 | Pettis | A61M 5/28 |
| | | | 604/117 |
| 2004/0097883 A1 | 5/2004 | Roe | |
| 2009/0069755 A1* | 3/2009 | Horvath | A61M 5/46 |
| | | | 604/240 |
| 2012/0296370 A1* | 11/2012 | Hansson | A61M 5/486 |
| | | | 606/202 |
| 2014/0018734 A1 | 1/2014 | Alchas et al. | |

FOREIGN PATENT DOCUMENTS

| | | |
|---|---|---|
| EP | 2853278 A2 | 4/2015 |
| JP | 2009-090098 A | 4/2009 |
| JP | 2011-212184 A | 10/2011 |
| JP | 2012-519546 A | 8/2012 |
| JP | 5008294 B2 | 8/2012 |
| WO | 2010102067 A2 | 9/2010 |
| WO | 2016123494 A1 | 8/2016 |

OTHER PUBLICATIONS

International Preliminary Report on Patentability dated Oct. 9, 2018 and Written Opinion of the International Searching Authority dated Jun. 27, 2017, which issued in corresponding PCT Patent Application No. PCT/US2017/026510.

Chinese Office Action dated Jul. 3, 2020, which issued in the corresponding Chinese Patent Application No. 201780031077.7, including English translation.

Japanese Office Action dated Mar. 30, 2021, which issued in corresponding Japanese Patent Application No. 2018-552673.

* cited by examiner

SYRINGE WITH A PATIENT CONTACT SURFACE

This application is a continuation application of U.S. Ser. No. 16/091,400, filed on Oct. 4, 2018, which was filed under 35 USC 371 from PCT/US2017/026510 filed on Apr. 7, 2017, which claims priority to U.S. Provisional Application Ser. No. 62/320,058, filed on Apr. 8, 2016, which is hereby incorporated by reference in its entirety.

BACKGROUND OF THE INVENTION

Field of the Invention

The invention is in the field of injection medical devices for delivering a medication or drug to a patient. Specifically the invention is directed to a syringe or pen needle having a needle-bearing hub with a patient-contacting surface for improved injection performance. The patient contacting surface is configured for promoting the desired depth of penetration of the cannula into the skin. The hub can be integral with the syringe barrel or can be installed on a medication pen used to administer medications, but is not limited to use with such devices.

Description of the Related Art

A medication pen for delivering self-administered medications generally comprises a syringe or a pen body, which houses a medication compartment, and a separate pen needle which may be attached to and detached from the pen body. The syringe or pen needle includes a needle-bearing hub having a recess on the proximal side for receiving the pen body and a proximal (non-patient end) needle accessing the medication compartment, typically piercing the septum of a medication cartridge in the pen body. The distal (patient-end) of the pen needle assembly includes the beveled distal end of the needle that is inserted into the injection site.

Injections may be performed in the intradermal (ID) region, the subcutaneous (SC) region and the intramuscular (IM) region. For many types of injectable medications, including insulin, the SC region is preferred for administering an injection. See, for example, Lo Presti, et al., Skin and subcutaneous thickness at injecting sites in children with diabetes: ultrasound findings and recommendations for giving injection, Pediatric Diabetes (2012).

Different length needles, and with increasing frequency, shorter needles such as 4 mm and 5 mm needles, are adapted to achieve injection to a specified target depth in a subcutaneous region. The present invention addresses the need to ensure that a needle is inserted to its target depth, regardless of the angle at which the user may approach the injection site with the medication pen.

In certain prior art pen needles the cannula is supported in an axially positioned post on the hub. The post forms a narrow portion extending distally from the relatively wider portion in which the pen body is received. In other pen needles known in the art, a distal face of the hub placed against the injection site may be relatively large, and may be provided with a slight taper at the edge. However, the edge of the hub engages the skin when the cannula is inserted at an angle, interfering with the injection.

While the prior devices are generally suitable for the intended use, there is a continuing need for improved devices for controlling the penetration of a cannula for delivering a drug or medicament.

SUMMARY OF THE INVENTION

The present invention is directed to an injection device and particularly to a syringe having needle hub with a skin contact surface configured for controlling the depth of penetration by a cannula extending from the needle hub. The invention is particularly directed to a needle hub device where the contact surface has a height and width that complement each other to control the depth of penetration of the cannula by providing a surface area sufficient to control the depth and shaped of the indentation in the skin under normal insertion forces.

The syringe of the present invention has a needle hub with a center post for supporting a cannula and an outer collar or ring surrounding the post. In one embodiment, the syringe is configured for dispensing small dosages of the contents in the range of about 0.3 ml to 0.5 ml although the volume can vary depending on the intended use of the injection device. In other embodiments, the syringe can deliver a volume of about 1 to 3 ml. The outer collar has a dimension to contact the surface of the skin during injection under typical insertion forces to control the depth of penetration of the cannula into the skin. The post has a distal end that can be positioned relative to the distal end of the collar to provide control in the depth of penetration of the cannula. The post can be positioned substantially flush with the distal face of the collar. In other embodiments, the distal end of the post can be spaced axially outward from the distal face of the collar a distance such that the distal face of the post and the distal face of the collar form a contact surface for contacting the skin and providing a shape and contour to control deformation of the skin when the cannula penetrates the skin during use. The dimensions and location of the post relative to the collar provide a skin contact surface having a dimension to distribute the force over the skin surface to reduce the incidence of the cannula penetrating the skin deeper than intended.

In one embodiment the hub of the syringe has a distal face with a diameter in a range of 2.0 mm to 8.0 mm. The distal face of the post can extend beyond the distal face of the collar whereby the distance between the distal face of the post and the distal face of the collar is about 1.0 to about 5.0 mm and generally about 0.3 mm to about 2.0 mm. In other embodiments, the distal face of the post can project from the distal face of the collar a distance of about 0.3 to 0.7 mm. In one embodiment, the distal end of the post can be aligned substantially flush with the distal end of the outer collar or recessed with respect to the collar.

Another aspect of the invention is a syringe having a needle hub defining a substantially convex skin contact surface defined by the post and the outer collar. The contact surface in one embodiment can have a height of about of 0.3 to 0.7 mm a surface area of 1-4 $mm^2$.

One feature of the invention is to provide a syringe having a center post for supporting the cannula and an outer collar surrounding the post where the distal end of the post is recessed with respect to the distal face of the collar about 0.3 to 0.7 mm. The hub can have a diameter or width of about 2.0 to 8.0 mm to provide sufficient surface area and a suitable shape to provide the controlled depth of penetration by the cannula into the skin. The distance between the distal face of the post and the distal face of the collar allows the skin of the patient to enter the recess that is defined by the recessed post where the skin contacts the post and the face of the collar.

A shape of the needle hub of the syringe provides a greater surface area contacting an injection site on a patient compared to a conventional syringe needle hub and controlling the depth of penetration of the cannula and reducing the occurrence of excessive penetration of the cannula. Greater patient comfort and stability are achieved as a result of a larger surface area contacting the skin during injection.

The various aspects and features of the invention are basically attained by providing an integral syringe comprising, a syringe barrel having an open proximal end configured for receiving a plunger, and distal outlet end. A post extends axially from said distal end of the syringe barrel, where the post has an axial passage communication with a cavity of the syringe barrel. A cannula is received in the axial passage of the post and extends from the distal end of the syringe barrel, where the cannula has a beveled distal end for injection into a subject's skin. An outer annular collar surrounds the post and extends axially from the distal end of the syringe barrel and defines an annular cavity between the post and the collar, where the collar has a distal end positioned relative to the distal end of the post to contact the skin upon insertion of the cannula into the skin of the patient.

The features of the invention are further attained by providing a syringe, comprising a syringe barrel having a medication compartment, a proximal end having a plunger and a distal end having a hub. The hub has an axially extending post with a distal annular face and an axial passage receiving a cannula and communicating with the medication compartment. An axially extending annular collar surrounds the post and has a distal annular face. The distal annular face of the post and the distal annular face of the collar are configured for forming a skin contact surface to control deformation of skin of a patient when contacting the skin with a normal insertion force and to control the depth of penetration of said cannula upon insertion of the cannula into the patient.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawing in which.

DETAILED DESCRIPTION OF THE INVENTION

Figure 1:
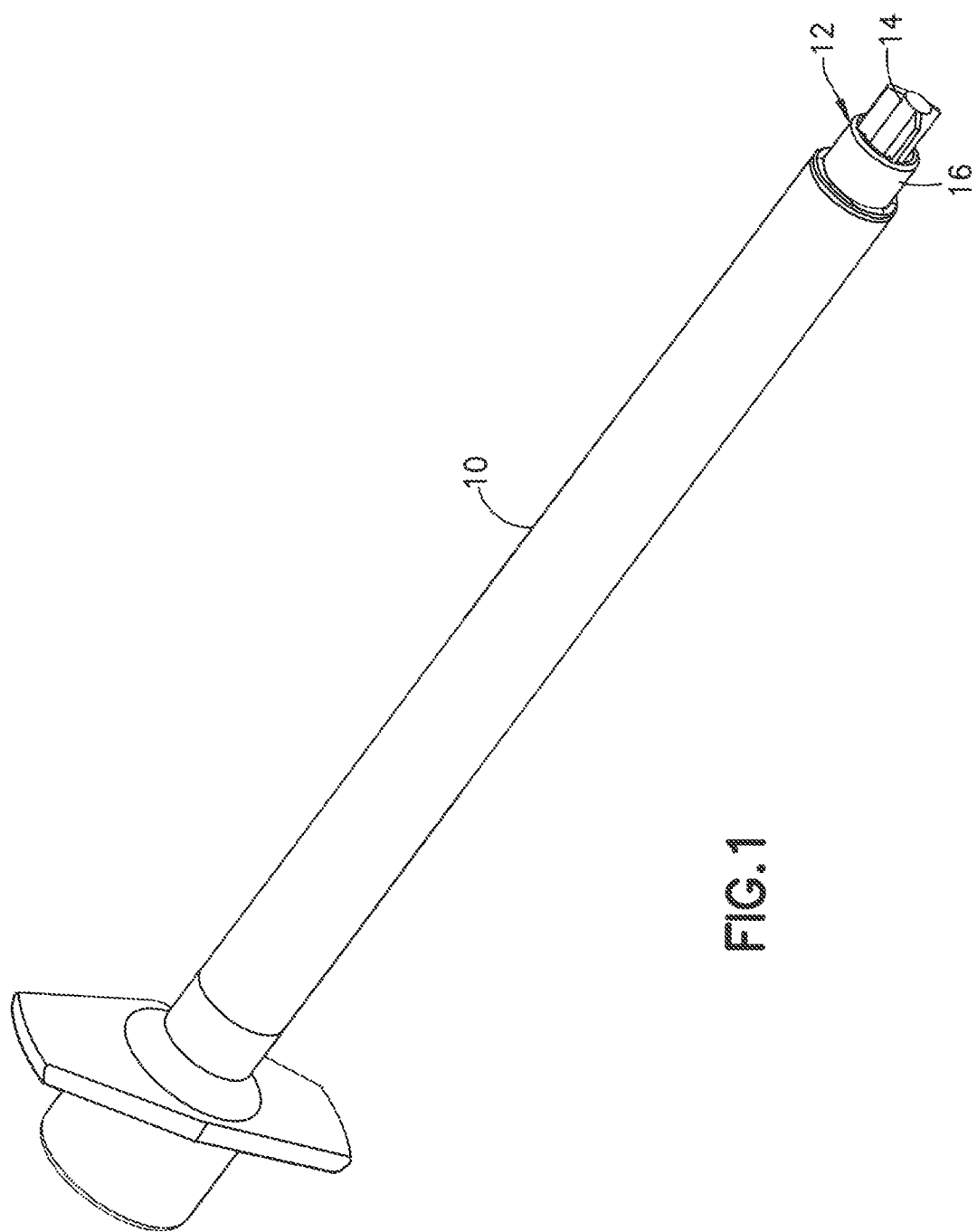
FIG. 1 depicts a standard syringe barrel having a needle hub protruding from the end of the syringe barrel.

A syringe is used herein to refer to a device having a medication compartment and a cannula for delivering the medication, such as insulin, to a patient. A pen delivery device typically contains multiple doses of medication, and a separate pen needle. The phrase "pen needle" refers to a needle-bearing assembly which can be attached to the medication pen body so that a proximal end of the pen needle assembly accesses a medication compartment and a distal end is adapted for insertion into an injection site to perform one or more injections. The terms "needle" and "cannula" can be used herein interchangeably. In one embodiment, the cannula can be a member configured for insertion into an injection site on a subject. One example is a cannula having a beveled end for insertion into the patient. As used herein, the "distal" direction is in the direction toward the injection site, and the "proximal" direction is the opposite direction. "Axial" means along or parallel to the longitudinal axis of the needle and the "radial" direction is a direction perpendicular to the axial direction.

The position of the subcutaneous layer in a subject's tissue and the desired injection depth vary depending on the age of the patient, the part of the body where the injection is administered, etc. Therefore, an injection depth in absolute terms cannot be considered a critical aspect of the invention. In general, the intradermal (ID) layer in adults has a thickness of around 2 to 3 mm, so that ID injection depth is in a range of about 3 mm or less, depth being measured from the outer surface of the skin. The subcutaneous (SC) region thickness can vary widely depending on the location of the injection site on the subject's body and the subject's body mass index (BMI). The average thickness of the SC space is in the range of about 7 mm to about 12 mm, so that SC injection depth is in a range of about 3 to 15 mm. The SC region may be further subdivided into the shallow subcutaneous (SSC) layer, having a thickness of about 1 mm, and an injection depth of about 2 to about 4 mm, the SC layer having a thickness of about 4 mm, at a depth of about 3 to 7 mm, and the deep subcutaneous (DSC) layer, having a thickness of about 4 mm, and a depth of about 7 to about 12 mm. If injections from a device occur in the upper region of the subcutaneous space (SSC), it is more likely that an ID injection will occur with that device. When injections from a device occur in the deeper regions of the subcutaneous space (DSC), it is more likely that an IM injection will occur with that device. Insulin is preferably delivered to the SC space. Injections to either the ID or intramuscular (IM) space may result in different uptake of insulin from what is prescribed.

The invention is directed to an injection device and particularly a syringe having a cannula with a predetermined length for penetrating the skin to a predetermined penetrating depth. The injection device has a skin contact surface for contacting and deforming the skin when the cannula penetrates the skin to assist in controlling the depth of penetration at various angles of injection with respect to the surface of the skin. The contact surface has a predetermined shape, width, and height to control the depth of penetration into the skin to the desired layer of the skin. In one embodiment, the contact surface having a diameter of about 3-4 mm provides a surface or contact area sufficient to prevent a deep indentation in the skin around the cannula when the device is pressed against the skin by a typical insertion force during use. The syringe can be, for example, a 0.3 ml syringe or a 0.5 ml syringe although over sizes can be provided depending on the drug being dispensed.

Figure 2:
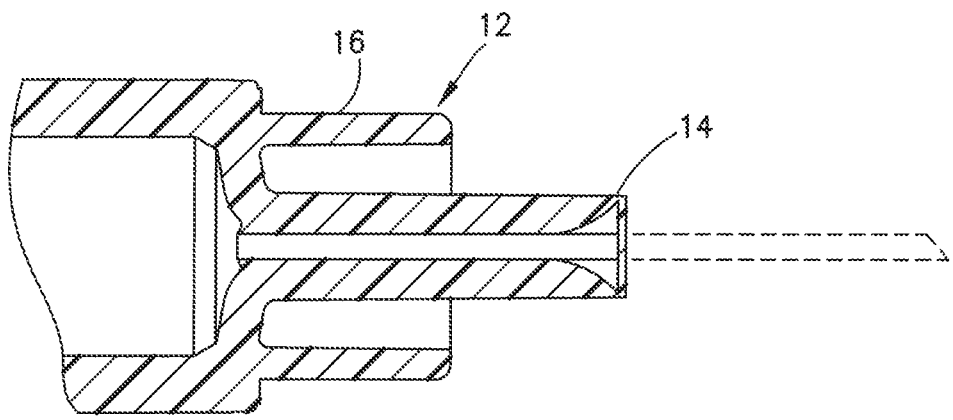
FIG. 2 is a cross sectional view of the needle hub of FIG. 1.

Referring to FIGS. 1 and 2, a commonly used syringe barrel 10 has a hub 12 with a post 14 projecting outward from the annular ring 16. The end face of the post is positioned from the outer ring 16 so that during normal use only the end of the post contacts the skin during the insertion of the cannula. The end face of the post has a dimension where a deep indentation is normally formed in the skin by the post contacting the skin. The deep indentation formed in the outer surface of the skin often results in the cannula penetrating deeper into the skin to skin layers deeper than intended by the user. By way of example, a 4.0 mm cannula mounted in a post having a width of about 1 mm can result in the contact surface forming a deep concave depression in the surface of the skin so that the cannula can penetrate the deeper than 4 mm and penetrate the deeper layers of the skin that can cause pain or discomfort to the user. The deeper penetration can also cause the cannula to deliver the drug to layers of the skin that are less effective in delivering the drug to the patients and increase the risk of intramuscular injection, particularly in pediatric patients.

In the invention, the skin contact surface of the syringe hub surrounding the cannula has a width and height configured for providing a larger surface area and greater control of the depth of penetration by the cannula. In one embodiment of the invention, the pen needle device is configured to obtain a cannula penetration of about 4 mm. The skin contact surface is further configured to control the shape, width and depth of deformation of the skin surface when the device is pressed against the skin during the penetration of the cannula. The width is determined as being the surface area defined by the outer peripheral edge that contacts the skin during the insertion of the cannula and during the injection or delivery of the drug using a normal insertion force. The height refers to the linear distance between the outer peripheral edge of the contact surface and the proximal end of the contact surface.

The skin contact surface in one embodiment of the invention can have a substantially convex shape, a substantially flat face, or concave face that contacts the skin during penetration of the cannula and delivery of the drug. The contact area can have a width or diameter of greater than 3.0 mm and typically about 4.0 mm. The contact area in one embodiment can have a substantially annular or circular shape. The width of the contact area refers to the diameter or transverse dimension of the outer peripheral edge as indicated by arrow 59 in FIG. 5. The contact area can be flush or can have height or depth of about 0.5 to about 1.5 mm measured from the outer peripheral edge of the contact surface to the contact surface of the post.

In the embodiment of FIGS. 3-7, the syringe 20 includes a syringe barrel 22 having an open proximal end 24 and a distal end 26. An internal axial cavity 28 shown in FIG. 5 receives the medicament to be delivered to the patient. The open proximal end 24 receives a plunger 30 for dispensing the contents of the syringe. A hub 32 extends axially from the distal end 26 for supporting a cannula 34 and defining the skin contact area.

Figure 4:
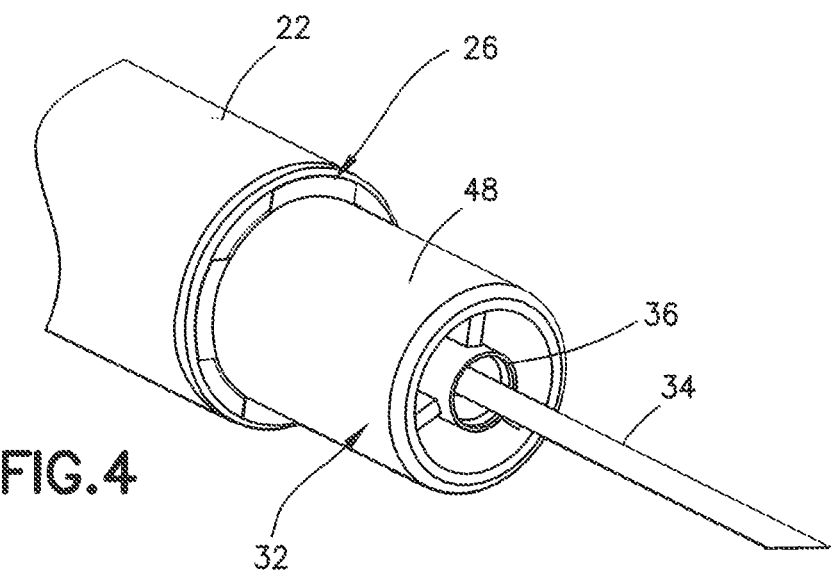
FIG. 4 is an enlarge partial perspective view of the syringe hub of FIG. 3.
Figure 3:
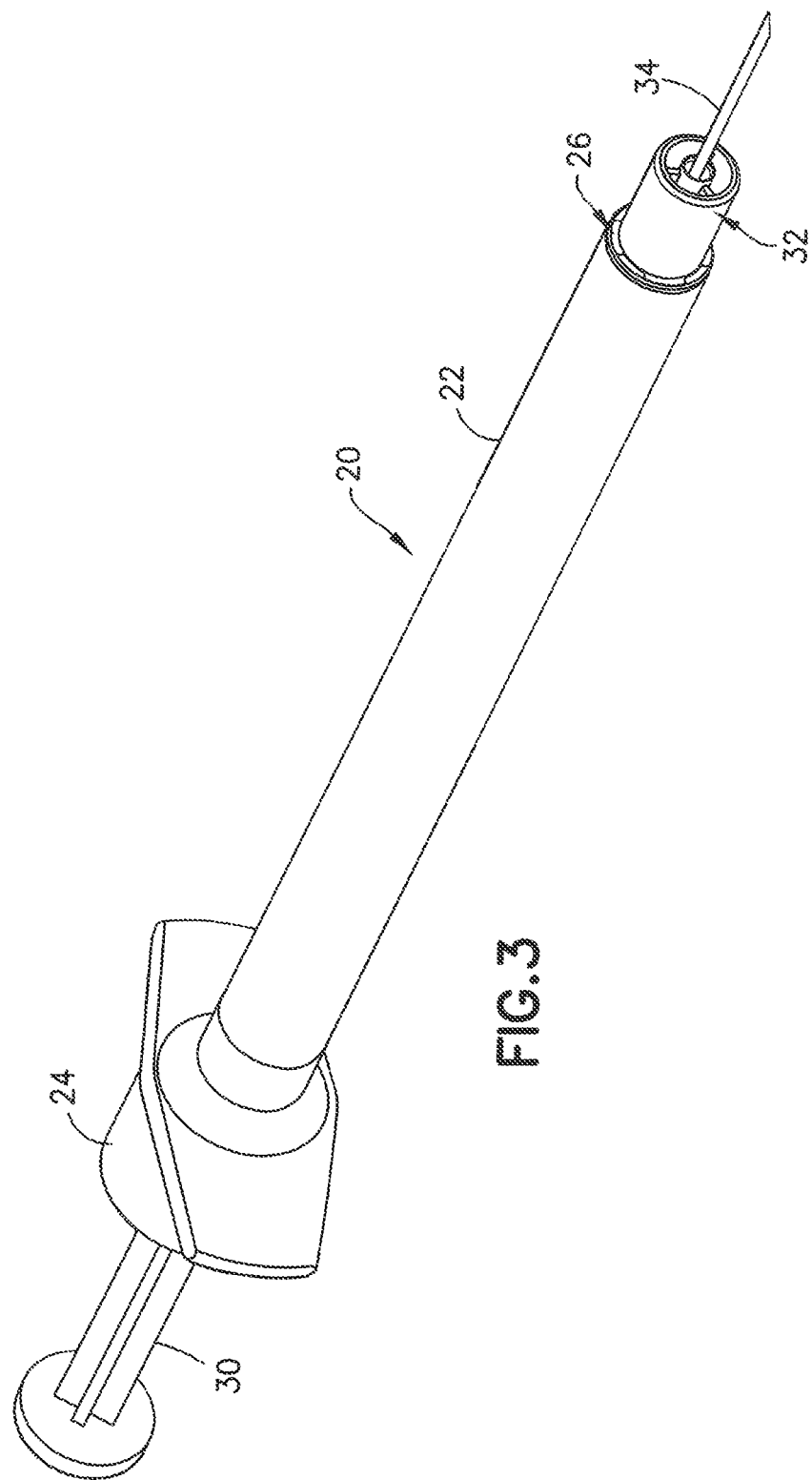
FIG. 3 is a perspective view of a syringe in a first embodiment of the invention showing the post substantially flush with the end of the collar.
Figure 5:
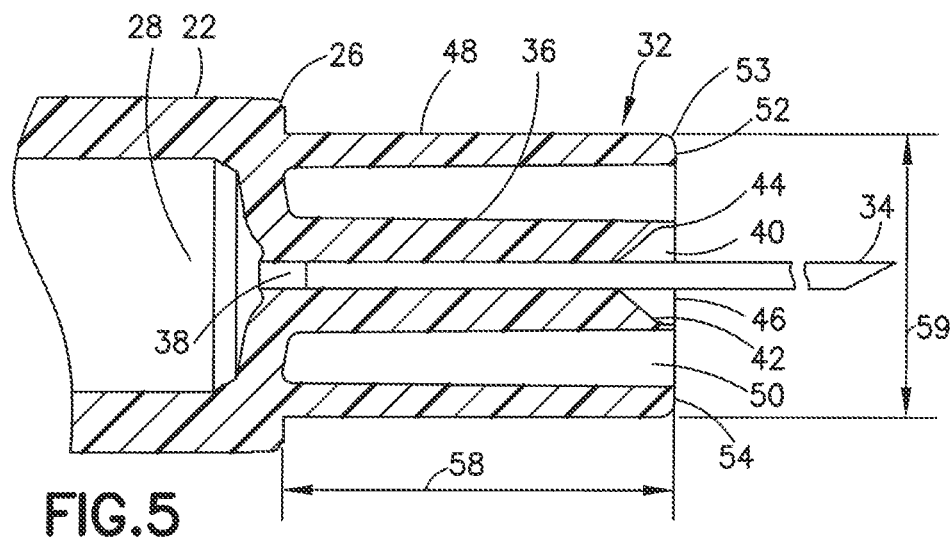
FIG. 5 is a cross sectional view of the syringe hub of FIG. 3.

The hub 32 shown in FIGS. 4 and 5 has a center post 36 extending axially for supporting the cannula 34. As shown in FIG. 5, the post 36 has an axial passage 38 communicating with the cavity 28 of the syringe barrel 22. The cannula 34 is mounted in the axial passage 38 and attached by a suitable adhesive 40 as shown in FIG. 5. The cannula 34 has a longitudinal length to penetrate the skin to the desire depth. The distal end of the axial passage 38 has a conical shape that flares outward toward the peripheral edge of the post to define a recess 42 for receiving the adhesive 40. In the embodiment show, the adhesive 40 fills the conical recess 42 so that axial end of the post is substantially flat and the adhesive does not protrude outward from the face of the post 36. The distal end face 44 of the post 36 in the embodiment shown has a substantially flat surface oriented in a plane substantially perpendicular to the longitudinal axis of the syringe and the cannula 34. The distal end face 44 in the embodiment shown has an annular configuration and narrow radial width relative to the diameter of the post 36. The adhesive 40 fills the recess 42 so that the adhesive is substantially flush with the peripheral edge of the post 36 to form a flat distal surface 46 for contacting the skin during the insertion of the cannula into the patient.

The hub 32 includes an outer annular collar 48 forming a sleeve or ring surrounding the post 36. The collar 48 is concentric with the post and spaced radially outward from the post 36 to define an annular recess 50. In the embodiment shown, the annular recess 50 extends from the proximal end of the collar 48 and the proximal end of the post 36 and extends between the outer surface of the post 36 and the inner surface of the collar 48. The radial dimension of annular recess 50 can be about 0.5 to 3 mm and typically about 1.0 mm.

The collar 48 has a distal face 52 forming an annular shaped skin contact surface spaced outward from the distal surface of the post 36. In the embodiment shown, the distal face 52 is substantially flat and is coplanar with the plane of the distal face 44 of the post 36. Distal face 52 has a slightly rounded peripheral edge 53 to provide a level of comfort to the patient during use. The distal face 44 of the post 36 and the distal face 52 of the collar 48 define a skin contact surface when the cannula is inserted into the patient. The distal face 52 of the collar 48 defines the outer dimension of the skin contact surface. The orientation and dimension of the collar 48 are provided to contact the skin of the patient under a typical insertion and injection force and to distribute the force over an area to control the depth of penetration of the cannula into the skin.

Figure 6:
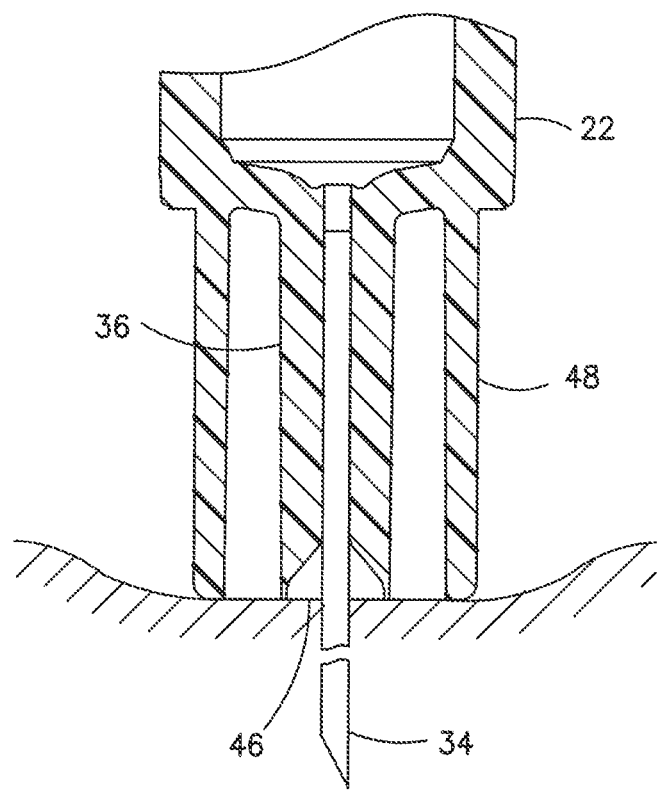
FIG. 6 is a cross sectional view of the syringe hub of FIG. 3 deforming the skin by the penetration of the cannula.

Referring to FIG. 6, the cannula 34 is inserted into the patient to penetrate the skin to the desire depth. The collar 48 has a diameter to disperse or distribute the penetration force over a larger surface area of the skin to limit the inward deforming or depression of the skin compared to the prior syringe where only the post supporting the cannula engages the skin that forms a deep depression or indentation in the skin resulting in a deep penetration of the cannula. The distal face 44 of the post 36 and the distal face 52 of the collar 48 define a substantially flat contact surface to distribute the force over a sufficient surface area to control the depth of the indentation formed by the penetration force as shown in FIG. 6.

The initial penetration of the cannula by the contact of the hub projecting from the syringe barrel with the skin of the patient forms a depression in the skin and an initial cannula penetration depth. The surface of the skin then relaxes as shown in FIG. 6 so that the surface of the skin conforms substantially to the shape of the contact surface and limits the depth of penetration of the cannula. The invention is directed to the shape, surface area and height of the contact surface to provide control of the depth of penetration of the cannula during the insertion and penetration force being applied to the injection device.

The cannula in the embodiment shown can have a length of about 4.0 to 6.0 mm to penetrate the skin to the desired depth for the efficient delivery of the drug and particularly insulin. In other embodiments, the cannula can have length of about 3.5 to about 8.0 mm. In still further embodiments, the cannula can have a length of about 2.5 to 6.0 mm and generally about 4.0 to 5.0 mm. The cannula can be, for example, a 31 gauge or 32 gauge although other gauges can be used. The contact surface of the hub has a width and height to control the deformation and dimension of the indentation in the skin and distribute the injection force across a sufficient area thereby controlling the depth of penetration of the cannula. The shape and dimension of the contact surface distribute the applied pressure upon full engagement to the skin surface. The contour in combination with the pressure distribution provides improve comfort to the patient. The height and surface area of the hub and the perimeter surface area influence the degree of compression and relaxation of the tissue for a given application force.

The dimensions of the hub can vary depending on the desired depth of penetration of the cannula and the length of the cannula. The collar has an axial length indicated by arrow 58. The collar can have a length of about 5.0-7.0 mm and typically about 6 mm. The collar can have a diameter indicated by arrow 59 of about 4.0 to 10.0 mm, generally about 3.0-5.0 mm and typically about 4.0 mm. The post 36 can have a diameter of about ⅓ the outer diameter of the collar. The post can have a diameter of about 1.0 to 2.0 mm.

Figure 7:
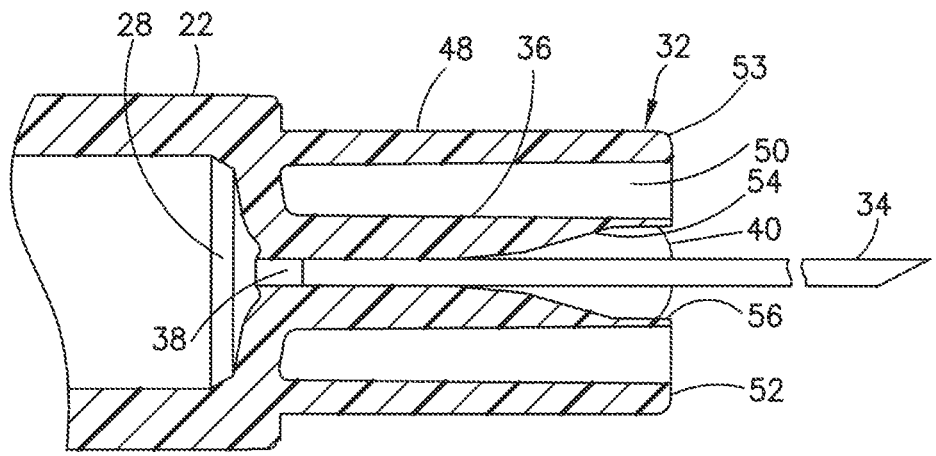
FIG. 7 is a cross sectional view of a modified syringe hub.

In another embodiment shown in FIG. 7, the post 36 can have a deep recess 54 at the distal end of the axial passage 38 to receive the adhesive and secure the cannula 34 to the post. In this embodiment, the recess 54 is sufficiently deep to allow the adhesive 40 to be recessed with respect to the distal end of the post and form a recess 56 around the cannula 34.

Figure 8:
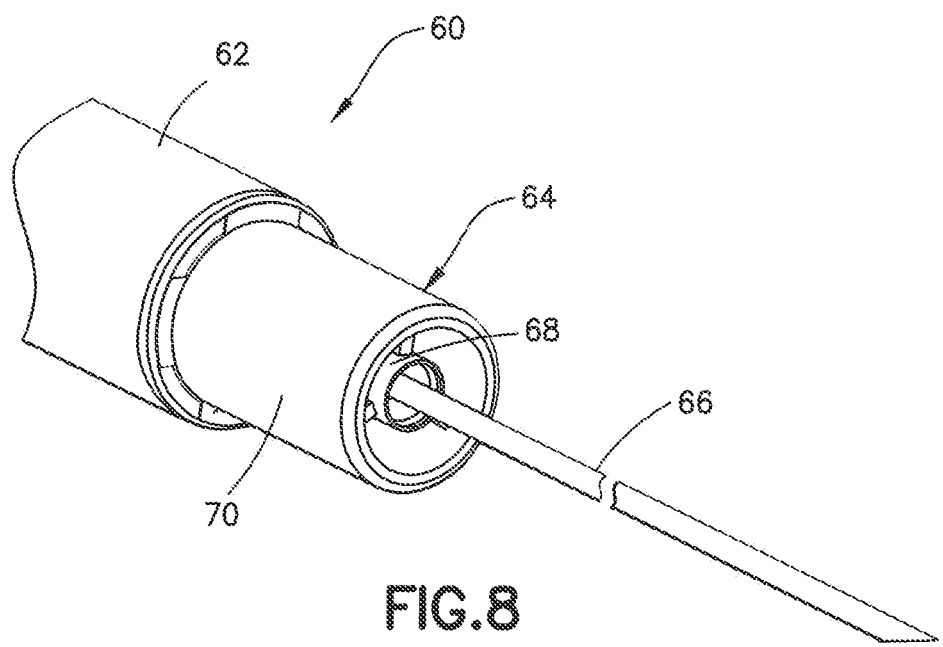
FIG. 8 is a perspective view of a syringe hub in another embodiment of the invention.
Figure 9:
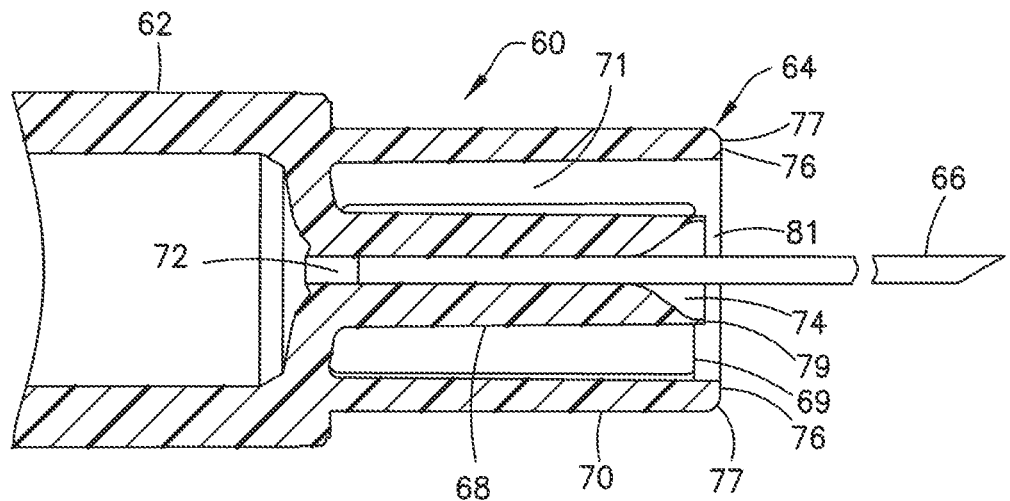
FIG. 9 is a cross sectional view of the syringe hub of FIG. 8.
Figure 10:
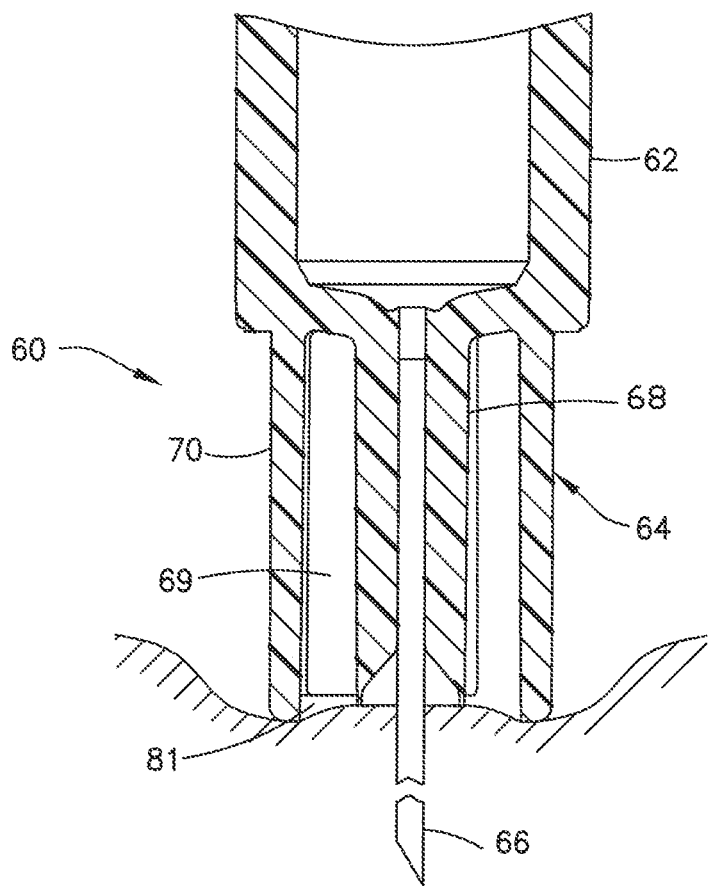
FIG. 10 is a cross sectional view of the syringe hub of FIG. 8 showing the deformation of the skin during the penetration of the cannula.

FIGS. 8-10 show an alternative embodiment of a syringe 60 having a syringe barrel 62 and a hub 64 for supporting the cannula 66. The hub 64 is formed by a center post 68 and an outer collar 70. The post 68 as in the previous embodiment has a substantially cylindrical shape that extends axially from the distal end of the syringe barrel. The post 68 has an axial passage 72 for receiving the cannula 66 and adhesive 74 to secure the cannula 66 to the post 68. The distal end of the post and the adhesive 74 define the distal face of the post for contacting the skin during the insertion of the cannula into the patient. In the embodiment shown, ribs 69 extend between center post 68 and outer collar 70 to stabilize the post 68 and cannula 66. As shown, ribs 69 have a distal end spaced inwardly from the distal end of post 68.

The collar 70 has a cylindrical shape surrounding the post and extends from the distal end of the syringe barrel to define an annular recess 71. The annular recess 71 can have a radial width of about 1-3 mm. The collar 70 has distal surface 76 forming an annular skin contact surface. In the embodiment shown, the distal surface 76 has a substantially flat contact surface oriented in a plane parallel to the plane of the distal face of the post and substantially perpendicular to the longitudinal axis of the cannula. The collar has an outer peripheral edge 77 that is rounded or curved to form a smooth transition between the distal face and the side surface of the collar. The distal surface 79 of the post 68 is recessed with respect to the distal surface 76 of the collar to form a slight recess 81. As shown in FIG. 10, the recess 81 formed by the position of the distal surface of the post 68 relative to the distal surface of the collar 70 allows the skin 83 of the patient to deform into the recess 81 during the insertion of the cannula into the skin of the patient. The distal surface of the post and the distal surface of the collar form the skin contact surface and have a radius to define a surface area to control the depth of the indentation in the skin under the insertion force. FIG. 10 shows the deformation of the skin during insertion of the cannula where the depression in the skin conforms substantially to the shape of the contact surface of the post and the collar.

In one embodiment, the axial spacing between the distal face 76 of collar 70 and the distal face 79 of post 68 can be about 1.0 to 1.5 mm and generally about 0.3 to 0.7 mm. The axial spacing between the distal face 76 of collar 70 and the distal face 79 of post 68 defines the depth of recess 81. The diameter of the inner edge of collar 70 defines the width of access 81.

Figure 11:
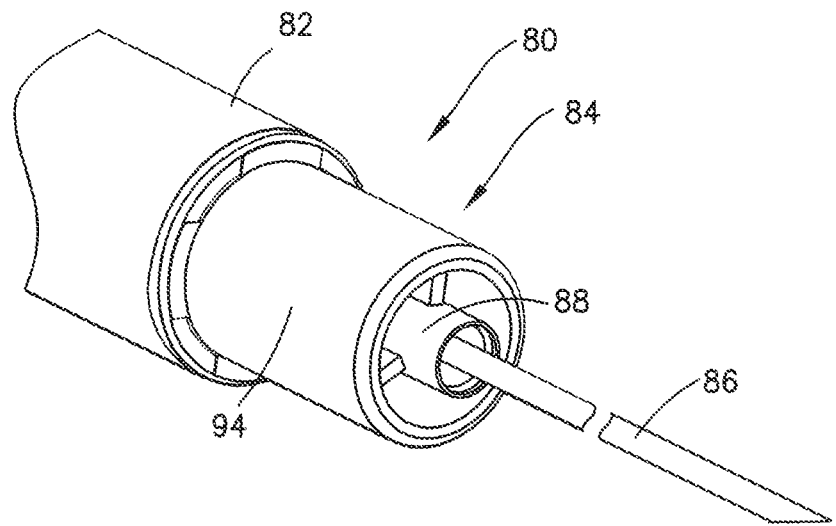
FIG. 11 is a perspective view of the syringe hub in another embodiment of the invention.
Figure 12:
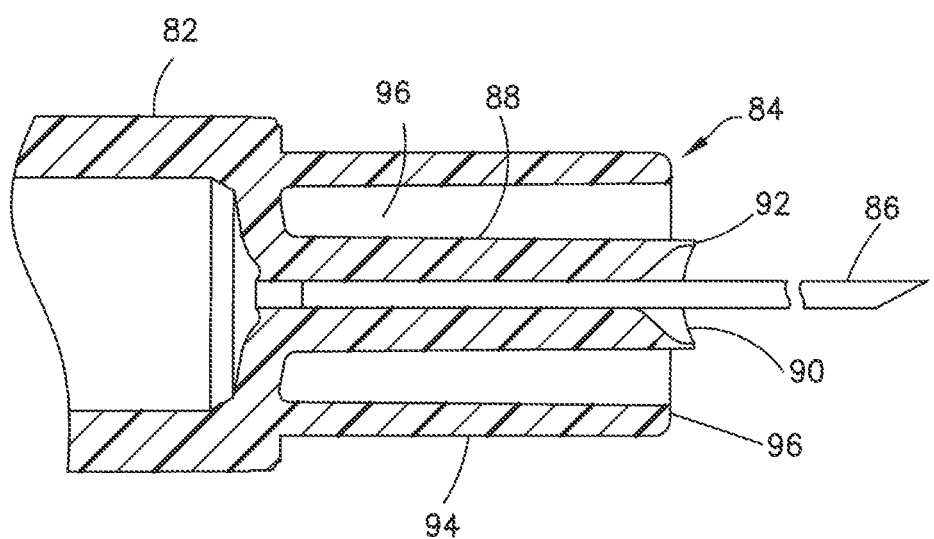
FIG. 12 is a cross sectional view of the syringe hub of FIG. 11.
Figure 13:
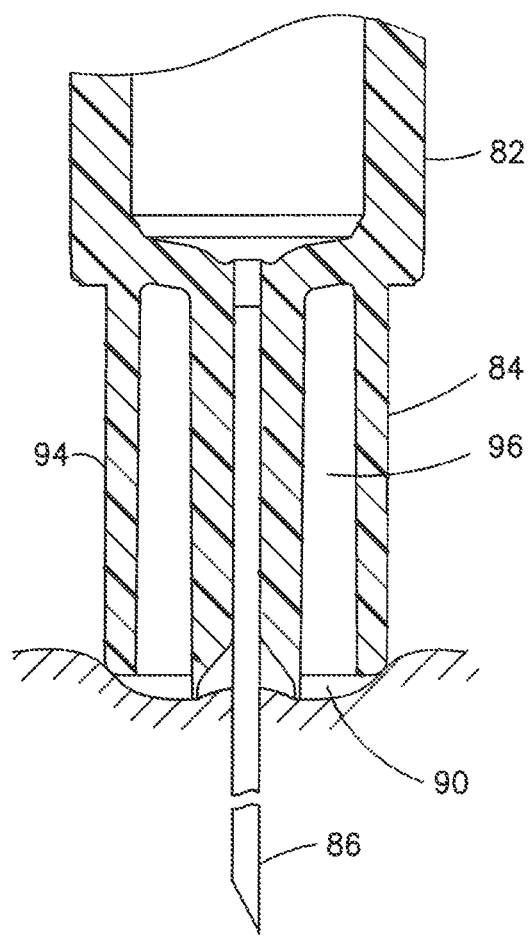
FIG. 13 is a cross sectional view showing the cannula insertion into the skin and the deformation of the skin.
Figure 14:
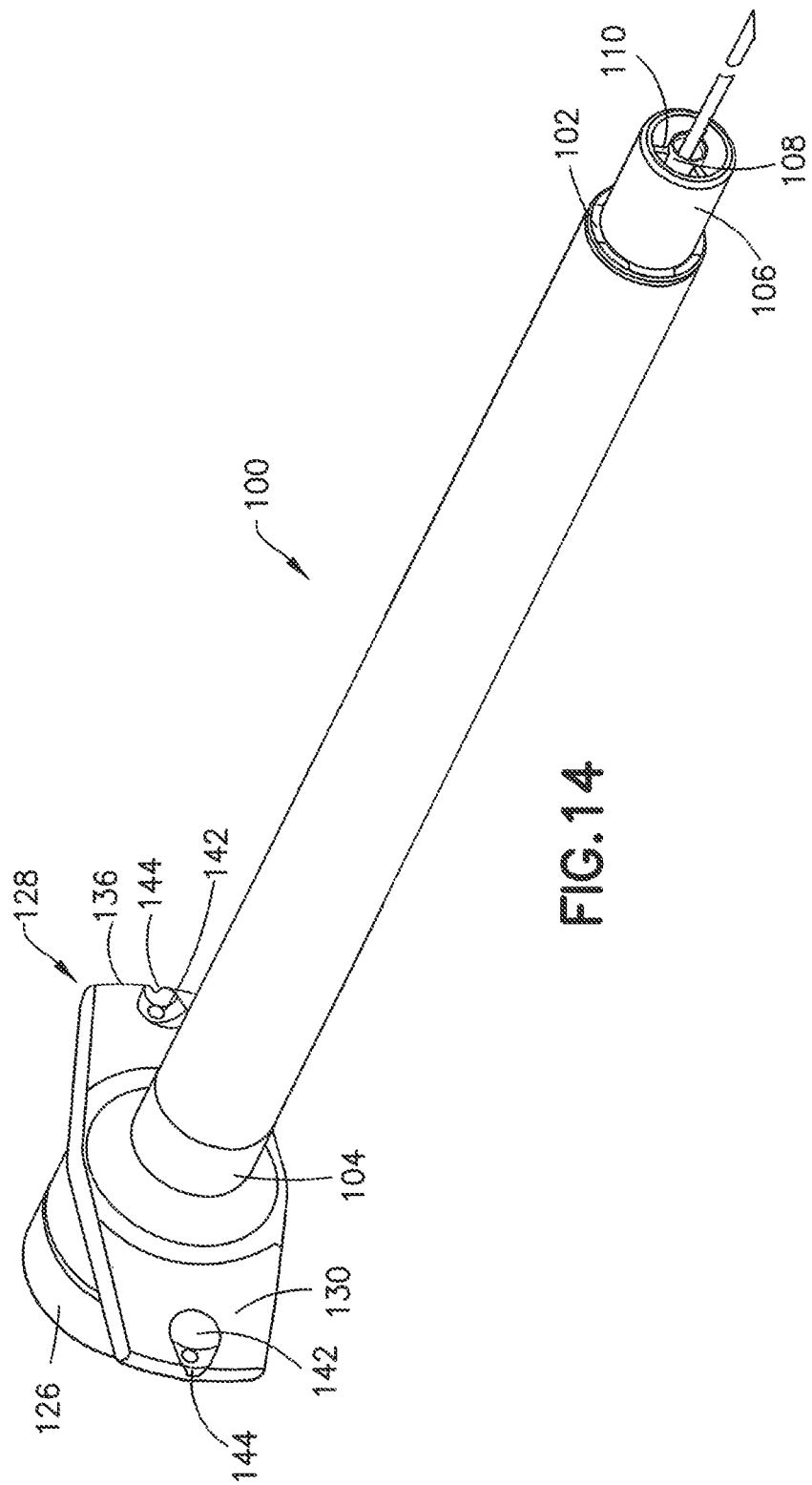
FIG. 14 is a perspective view of another embodiment of the syringe device.

FIGS. 11 to 13 show another embodiment of a syringe 80 having a syringe barrel 82 and a hub 84 supporting a cannula 86. The hub 84 has a center post 88 for receiving the cannula 86 and a conical shaped recessed end receiving the adhesive 90. As in the previous embodiment, the adhesive fills the recess in the end of the post 88 to form a substantially flat distal face 92 of the post 88. An outer collar 94 surrounds the post 88 to define an annular recess 96 between the post 88 and the collar 94. Annular recess 96 can have a radial width extending between the inner face of collar 94 and outer face of post 88 of about 0.5 to 3.0 mm and typically about 1.0 mm.

In the embodiment of FIG. 12, the post 88 has an axial length greater than an axial length of the collar 94 so that the distal surface 92 of the post 88 is spaced axially outward from the distal surface 96 of the collar. As shown in FIG. 13, the post 88 is spaced from the collar a distance so that the distal surface of the post and the distal surface of the collar define a skin contact surface during the insertion of the cannula. The distal surface of the post produces a depth of the resulting indentation greater than the depth of the collar and provides a smooth substantially concave curvature of the skin indentation as shown in the FIG. 13. The skin deformation is caused by the insertion force during the insertion and penetration of the cannula using an insertion force normally applied by the patient. In one embodiment, the distal face 92 of post 88 can extend axially from the distal face of collar 94 a distance of about 0.3 to 0.7 mm. In the embodiment shown, the post 88 and collar 94 form a substantially convex curved skin contact surface. The post 88 can extend from the collar a distance to provide, for example a skin contact surface with a radius of curvature of about 6.0 to 10.0 mm.

The distal contact face of the hub can have various configurations for providing the desired control for the depth of penetration of the cannula. In each embodiment, the distal contact face has a width or diameter to provide a sufficient surface area and height defined by the curvature of the contact face to minimize the depressing of the skin that can cause the cannula to penetrate the skin deeper than intended.

In various embodiments, the post can have a diameter of about 1.0-3.0 mm and generally about 1.0-1.5 mm. The post can have a height of about 1.0-1.5 mm as measured from the outer periphery of the contact surface of the collar. The ratio of the diameter (D) of the post to the axial spacing between the distal face of the post and the distal face of the collar can range from about 2:1 to about 4:1 and generally about 2.5:1 to 3:1. The larger ratio provides a greater surface area that provides increased comfort to the patient and greater control of the insertion depth.

Figure 15:
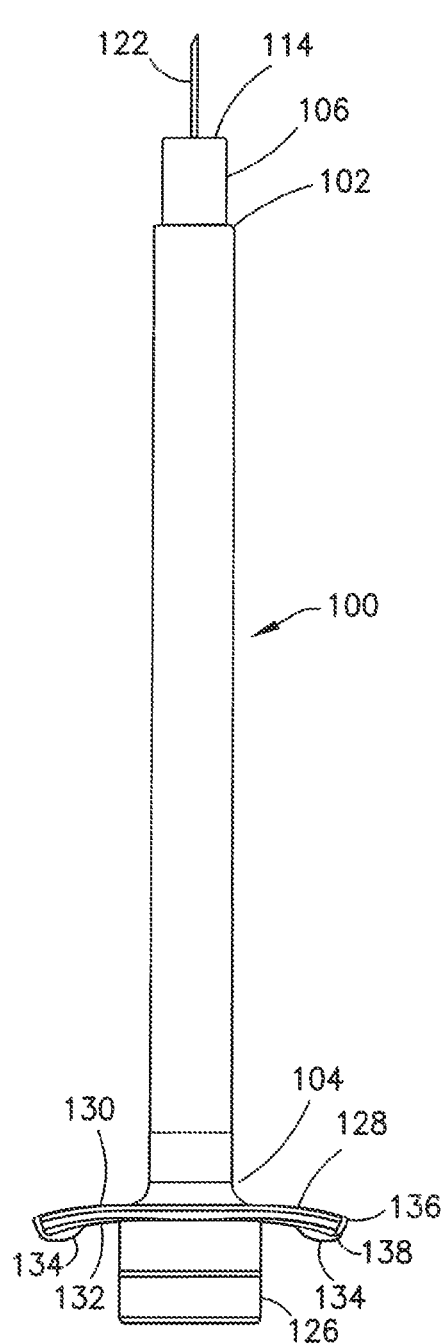
FIG. 15 is a side view of the syringe of FIG. 14.
Figure 16:
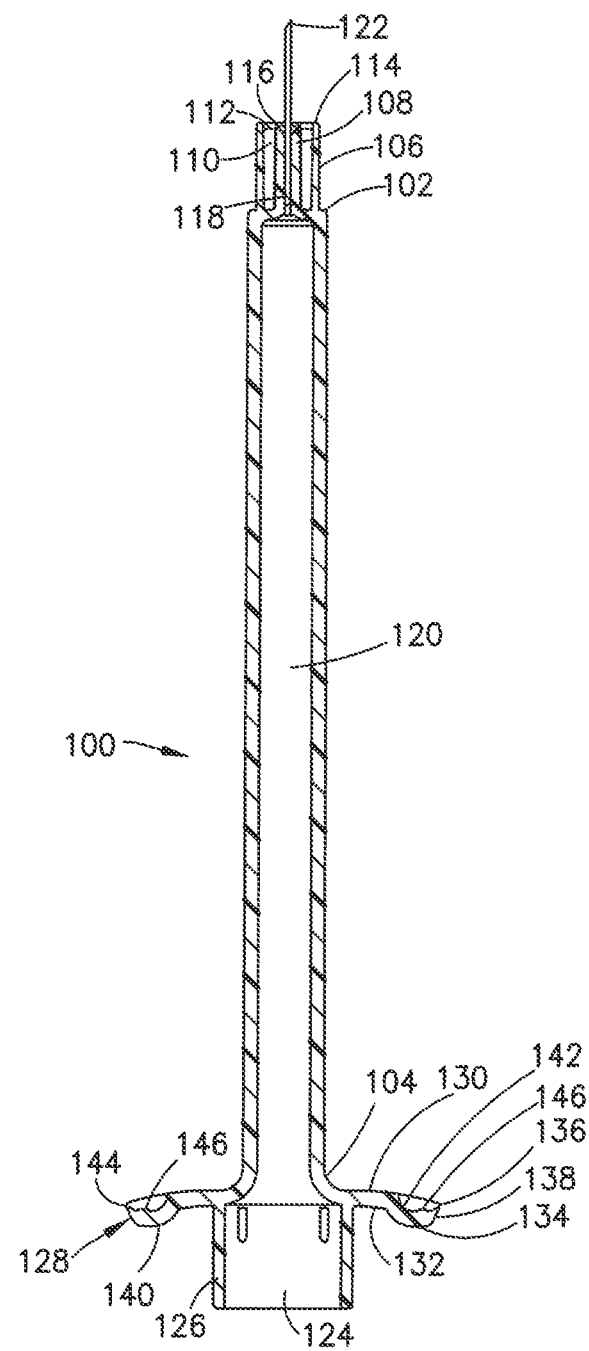
FIG. 16 is cross sectional view of the syringe of FIG. 14.
Figure 17:
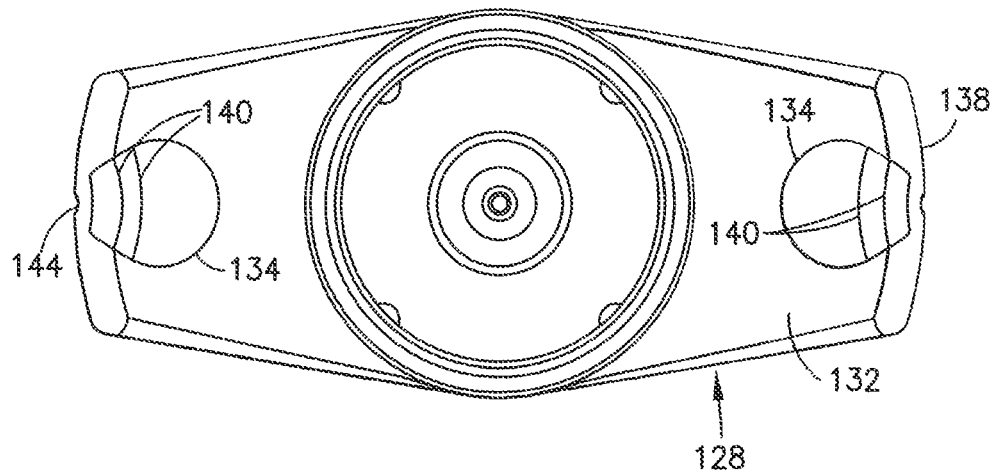
FIG. 17 is a top end view of the syringe of FIG. 14.

Referring to FIGS. 14-18 a further embodiment of the injection device is shown including a syringe barrel 100 having a distal end 102 and proximal end 104. Distal end 102 is similar to the embodiment of FIGS. 2-6 and includes an outer collar 106, an inner post 108 and radially ribs 110 extending between the inner surface of the outer collar 106 and the outer radial surface of the post 108. As shown in FIG. 16, the ribs 110 have a distal end 112 spaced from the ends of the collar 106 and the post 108. In this embodiment, collar 106 has an annular distal face 114 oriented in a plane substantially perpendicular to the longitudinal axis of the syringe barrel 100. Inner post 108 has a distal annular face 116 oriented in a plane substantially perpendicular to the longitudinal axis of the syringe barrel. In the embodiment shown, the distal face 116 of post 108 is oriented in the same plane as the distal face 114 of collar 106. A longitudinal passage 118 extends through post 108 for receiving and supporting a cannula 122 and communicating with the internal chamber 120 of syringe barrel 100. The cannula 122 is attached to the post 106 by an adhesive as in the previous embodiment and has a length and width as in the previous embodiments.

The proximal end 104 of syringe barrel 100 has an open end 124 for receiving a plunger (not shown) for dispensing the contents of the chamber 120 in the usual manner. In the embodiment shown, the proximal end 104 of the syringe barrel 100 has an axially extending collar 126 for receiving the operating end of the plunger.

Flanges 128 extend radially outward from opposite sides of the proximal end 104 between syringe barrel 100 forming finger grips or finger flanges for the user to operate the device and deploy the plunger during use. In one embodiment as shown in FIG. 15, the flanges 128 are substantially the same and mirror images of each other to extend outward for gripping the device by the user. In other embodiments, the flanges can be asymmetrical with different shapes, sizes and orientations to provide the desired tactile feel to assist the user in gripping and manipulating the device. The flanges 128 have distal surface 130 and a proximal surface 132. In the embodiment shown, the flanges 128 curve away from the distal end of the syringe barrel 100 to form a substantially concave surface of proximal surface 132. In alternative embodiments, the flanges can curve in the opposite direction toward the distal end of the syringe. As shown, the flanges 128 have curvature to provide an ergonomic grip and distinctive feel to increase conform to the user's fingers comfort of use. The ergonomic shape and conformation of the flanges 128 provide increased comfort and tactile confirmation that makes holding and handling of the syringe easier for people with dexterity issues, such as arthritis and neuropathy that can occur in diabetes patients. In other embodiments, one or both flanges can curve toward the distal end or can be straight and substantially flat.

In one embodiment, flanges 128 are provided with a tactile conformation to assist the user during deployment of the plunger and delivery of the substance. The tactile conformation can be on one or both flanges and on either or both distal surface and proximal surface. In the embodiment shown, a dimple 134 is formed in the flanges 128 to extend from the proximal surface of the flanges. In the embodiment shown, the dimple 134 is oriented toward the outer edge 136 of flange 128 forming a smooth curved portion 128 between the dimple 134 and collar 126. In other embodiments, the dimple can be positioned in the center or other locations of the flange surface or surfaces. Dimple 134 in the embodiment shown has a substantially convex, domed, tear drop shape where the outer edge 138 of the dimple is formed at the outer edge of 136 of the flange 128. Alternatively, the dimple can have other shapes, such as a rounded or oval shape. The dimple 134 has a width, length, and height sufficient to provide a tactile feel to assist the user in positioning and holding the syringe. In other embodiments, the dimples or other tactile member can be spaced inwardly from the end of the flanges and provided in other suitable orientations. In one embodiment, the dimples can extend the width or length of the flanges and provided on one or both surfaces of the flange.

Ridges 140 can be provided on the face of the dimple 128 to provide an additional tactile feel. In the embodiment shown, the ridges extend across the outer face of the dimple 134 and positioned toward the outer edge relative to the convex surface of the dimple 134. The ridges can be oriented to extend radially outward on the outer and/or inner surface of the dimples. In other embodiments, recess or other tactile conformations can be provided on the dimples in place of projecting ridges.

Figure 18:
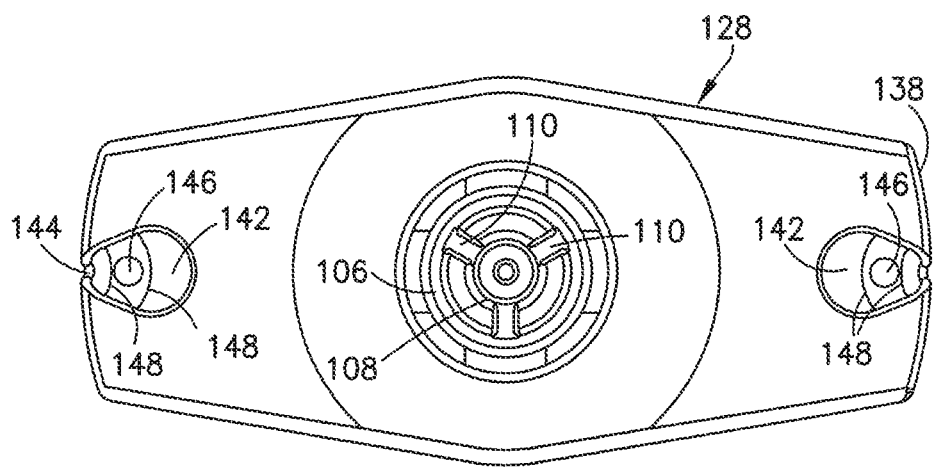
FIG. 18 is a bottom end view of the syringe of FIG. 14.

The dimple 134 forms a concave recess 142 on the distal surface 130 of the flange 128 as shown in FIG. 18. The recess 142 can also have one or more ridges or recesses in the surface to provide a tactile feel. A substantially U-shaped open portion 144 is formed along the outer edge to form a recess along the outer edge 136 to provide a tactile feel for the user. A detent 146 forming a projection is formed in the concave surface of the recess 142 that projects toward the distal end of the syringe barrel 100. As shown in FIGS. 16 and 18, ridges 148 can be formed adjacent the detent 146 to extend across the width of the concave recess 142. The detent 146 and ridges 148 provide an additional tactile feel for the user to assist in holding and positioning the syringe barrel. In other embodiments, ridges can provided to extend across the entire surface of proximal surface, the distal surface or both the distal and proximal surfaces.

Figure 19:
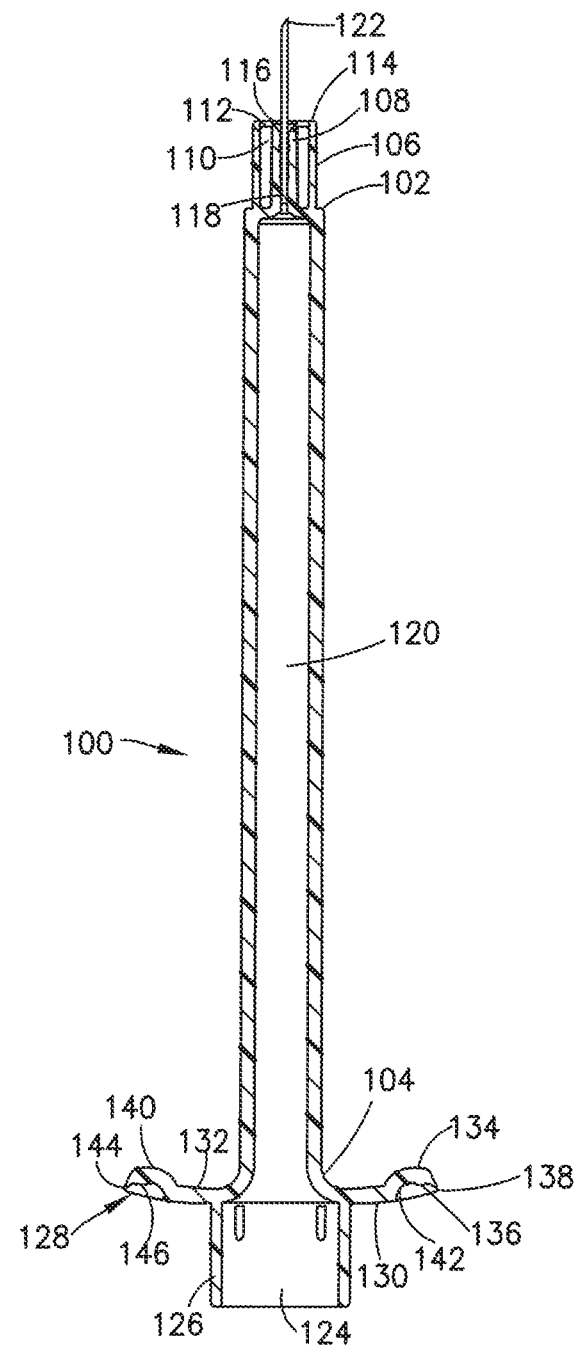
FIG. 19 is a cross sectional side view of the syringe in a further embodiment.

In the embodiment shown, the dimples project from the proximal surface. In alternative embodiments, the dimples can project from the distal surface to form a recess on the proximal surface. In other embodiments other tactile conformation or members can be provided on the proximal and/or distal surfaces to assist the user in positioning and manipulating the syringe. In a further embodiment shown in FIG. 19, the flanges 128 curve toward the distal end of the syringe. The elements of the embodiment of FIG. 19 are identified by the same reference numbers for consistency. In the embodiment of FIG. 19, the dimples 140 are shown projecting from the distal surface of the flanges toward the distal end of the syringe. The recesses 136 are shown being formed on the proximal surface of the flanges. In further embodiments, the dimples or other tactile member can project from the proximal surface of one or both flanges or from the distal surface of one or both flanges. In a similar manner, one or more recesses can be formed on one or both flanges on the proximal surface, the distal surface or both proximal and distal surfaces.

The dimples 134 in the flanges 128 are shown in connection with the embodiment where the inner post 108 has an axial length substantially the same as the axial length of the collar 106. The dimples 134 can also be included in the embodiment of FIGS. 3-7 and the embodiment of FIGS. 8-10 where the post 68 has an axial length less than an axial length of the collar 70 and in the embodiment of FIGS. 11-13 where the post 88 has an axial length greater than an axial length of the collar 94 to provide the desire tactile feel to the syringes during use.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

What is claimed is:

1. A one piece, integral syringe comprising,
   a syringe barrel having an open proximal end configured for receiving a plunger, and distal outlet end;
   a post extending axially from said distal end of said syringe barrel, said post having an axial passage communication with a cavity of said syringe barrel and a distal end face;
   a cannula received in said axial passage of said post and extending from said distal end of said syringe barrel, said cannula having a beveled distal end for injection into a subject's skin;
   an outer annular collar surrounding said post and extending axially from said distal end of said syringe barrel and defining an annular recess between said post and said collar, said collar having a distal end face positioned relative to said distal end face of said post a distance to define a radius of curvature of about 6.0 to 10.0 mm, whereby said distal end face of said collar and said distal end face of said post contact the skin and provide a controlled deformation of the skin for inserting the cannula to a selected depth and inhibit tenting of the skin around said cannula;
   wherein said syringe barrel further includes at least one flange extending radially outward from a proximal end of said syringe barrel for gripping by a user, said flange having a proximal surface with at least one tactile member, and a distal surface with at least one tactile member;
   wherein said tactile member on said proximal surface of said flange is a dimple projecting outward from said proximal surface and where said tactile member on said distal surface is a recess; and
   wherein said at least one recess in said distal surface includes a projecting detent.

2. The syringe according to claim 1, wherein said post has an outer diameter of 1.0 to 2.0 mm.

3. The syringe according to claim 1, wherein said distal end face of said post is spaced axially outward from said distal end face of said collar a distance whereby said distal end face of said post and distal end face of said collar define a skin contact surface.

4. The syringe according to claim 2, wherein said cannula has an exposed length of about 4.0 to 6.0 mm.

5. The syringe according to claim 1, wherein said cannula has an exposed length extending from said post of about 3.5 to about 8.0 mm and said distal end of said collar has a width of about 4.0 to about 10.0 mm.

6. The syringe according to claim 1, wherein said distal end face of said post has a radial width to contact the surface of the skin during insertion of the cannula into the skin of the patient, and said distal end face of said collar has an axial face oriented with respect to said post to whereby said distal end face of said post and said distal and face of said collar forms a skin contact surface with a configuration to distribute an insertion force and to control deformation of the skin upon insertion of the cannula into the patient.

7. The syringe according to claim 4, wherein said distal end of said post is spaced axially outward from said distal end of said collar a distance of about 0.3 to 0.7 mm and said skin contact surface has a diameter of about 3.0 to 4.0 mm.

8. The syringe according to claim 7, wherein said distal end face of said post is substantially flat and oriented in a plane substantially perpendicular to a longitudinal axis of said syringe barrel.

9. The syringe according to claim 8, wherein said distal end face of said collar is substantially flat and has an outer edge with a convex rounded profile, said flat surface extending between said outer edge and an inner edge where said flat surface is substantially parallel to said flat surface of said post.

10. The syringe according to claim 9, wherein said axial passage of said post has a conical shaped recess at said distal end of said post, and where an adhesive is received in said recess to attach said cannula to said post and where said adhesive is substantially flush with said distal end face to form a flat end surface forming said skin contact surface.

11. An integral syringe comprising,
    a syringe barrel having an open proximal end receiving a plunger, and distal outlet end;
    a post extending axially from said distal end of said syringe barrel, said post having an outer diameter of 1.0 to 2.0 mm and an axial passage in communication with a cavity of said syringe barrel and a distal end face;
    a cannula received in said axial passage of said post and extending from said distal end of said syringe barrel, said cannula having an exposed length of about 4.0 to 6.0 mm for injection into a subject's skin;
    an outer annular collar surrounding said post and extending axially from said distal end of said syringe barrel and defining an annular recess between said post and said collar, said collar having a distal end face positioned relative to said distal end face of said post a distance to contact the skin upon insertion of said cannula into the skin of the patient, whereby said distal end face of said collar and said distal end face of said post form a continuous curve having a radius of curvature of about 6.0 to about 10.0 mm to contact the skin and provide a controlled deformation of the skin for inserting the cannula to a selected depth, said syringe barrel, post and outer annular collar defining an integral, one-piece syringe;
    wherein said distal end face of said post is spaced axially outward from said distal end face of said collar a distance of about 0.3-0.7 mm whereby said distal end face of said post and distal end face of said collar define a skin contact surface, and where said skin contact surface has a diameter of about 3.0-4.0 mm, wherein said distal end face of said post has a radial width to contact the surface of the skin during insertion of the cannula into the skin of the patient, and said distal end face of said collar has an axial face oriented with respect to said post whereby said distal face of said post and said distal end face of said collar form a skin contact surface with a configuration to distribute an insertion force and to control deformation of the skin upon insertion of the cannula into the patient;

wherein said syringe barrel further includes at least one flange extending radially outward from a proximal end of said syringe barrel for gripping by a user, said flange having a proximal surface with at least one tactile member comprising a projection, and a distal surface with at least one tactile member comprising a projection; and wherein said at least one tactile member on said distal surface is a recess, and said recess includes a projecting detent.

12. The syringe according to claim 11, wherein said distal end face of said post is substantially flat and oriented in a plane substantially perpendicular to a longitudinal axis of said syringe barrel.

13. The syringe according to claim 12, wherein said distal end face of said collar is substantially flat and has an outer edge with a convex rounded profile, said flat surface extending between said outer edge and an inner edge where said flat surface is substantially parallel to said flat surface of said post.

14. The syringe according to claim 13, wherein said axial passage of said post has a conical shaped recess at said distal end of said post, and where an adhesive is received in said recess to attach said cannula to said post and where said adhesive is substantially flush with said distal end face to form a flat end surface.

15. An integral syringe comprising, a syringe barrel having an open proximal end configured for receiving a plunger, and distal outlet end with a hub extending from said distal end of said syringe barrel;

a post integrally formed with said syringe barrel and extending axially from said distal end of said syringe barrel, said post having an axial passage communication with a cavity of said syringe barrel and receiving a cannula, said post having a distal end with an annular recess around said cannula, said post having a substantially annular distal end face around said annular recess in said post with a dimension for contacting the skin of a patient during insertion of the cannula;

an outer annular collar integrally formed with said syringe barrel surrounding said post and extending axially from said distal end of said syringe barrel and defining an annular cavity between said post and said collar, said collar having a distal end face positioned relative to said distal end face of said post a distance to define a skin contact surface to contact the skin upon an insertion force applied to said syringe barrel and insertion of said cannula into the skin of the patient, whereby said distal end face of said collar and said distal end face of said post provide a skin contact surface sufficient to contact the skin and distribute the insertion force across the skin to provide a controlled deformation of the skin and inserting the cannula to a selected depth;

wherein said syringe barrel further includes at least one flange extending radially outward from a proximal end of said syringe barrel for gripping by a user, said flange having a distal surface with at least one tactile member comprising a projection extending from said distal surface, and a proximal surface with at least one tactile member comprising a projection extending from said proximal surface;

wherein said at least one tactile member on said distal surface is a recess, and said recess includes a projecting detent.

16. The syringe according to claim 15, wherein at least one of said distal surface and said proximal surface has a recess.

17. The syringe according to claim 15, wherein said post has an outer diameter of 1.0 to 2.0 mm, said cannula has an exposed length of about 4.0 to 6.0 mm, said annular distal end face of said collar forming a continuous curvature with a radius of about 6.0 to 10.0 mm, said post extends from said collar a distance of about 0.3 to 0.7 mm, and said skin contact surface has a diameter of about 3.0 to 4.0 mm.

* * * * *